United States Patent [19]
Rosen et al.

[11] Patent Number: 6,085,743
[45] Date of Patent: Jul. 11, 2000

[54] POLARIZED GAS DELIVERY SYSTEM/METHOD

[75] Inventors: Matthew S. Rosen; Scott D. Swanson; Kevin P. Coulter; Robert C. Welsh; Timothy Chupp, all of Ann Arbor, Mich.

[73] Assignee: The Regent of the University of Michigan, Ann Arbor, Mich.

[21] Appl. No.: 08/866,138

[22] Filed: May 30, 1997

[51] Int. Cl.[7] .................................................. A61M 16/00
[52] U.S. Cl. .............................. 128/200.24; 128/203.12; 128/201.21; 128/DIG. 27; 600/410; 600/529; 62/637
[58] Field of Search ........................ 128/200.24, 201.21, 128/203.12, 203.14, 203.25, 204.15, DIG. 27; 600/410, 529; 62/637, 919, 925

[56] References Cited

U.S. PATENT DOCUMENTS

| | | | |
|---|---|---|---|
| 5,007,243 | 4/1991 | Yamaguchi et al. | 62/51.1 |
| 5,039,500 | 8/1991 | Shino et al. | 423/262 |
| 5,099,834 | 3/1992 | Fishman | 128/203.12 |
| 5,357,959 | 10/1994 | Fishman | 600/420 |
| 5,617,859 | 4/1997 | Souza et al. | |
| 5,809,801 | 9/1998 | Cates, Jr. et al. | 62/637 |

*Primary Examiner*—John G. Weiss
*Assistant Examiner*—V. Srivastava
*Attorney, Agent, or Firm*—Harness, Dickey & Pierce, P.L.C.

[57] ABSTRACT

A system, and corresponding method, that interfaces with a gas polarization system to deliver a polarized noble gas to a subject for inhalation. Large volumes of polarized noble gas are obtained by repeated production/freezing cycles of a spin-exchange system. A storage cylinder is provided for storing a polarized noble gas. A gas delivery line is coupled to the storage cylinder and selectively delivers the polarized noble gas to the storage cylinder, and from the storage cylinder to the subject. A vacuum means is in communication with the gas delivery line for evacuating the storage cylinder in the gas delivery line prior to the noble gas being delivered thereto. A plurality of non-metallic gas delivery valves, located between the gas delivery line and the vacuum means, selectively control communication between the vacuum means and the polarized noble gas to minimize depolarization of the polarized noble gas during delivery of the noble gas to the subject on a breath-by-breath basis, or at a constant delivery rate. Control of remotely activated pneumatic valves allows complete automation of the polarization/accumulation/storage/delivery cycle for use in a low maintenance commercial device suitable for clinical and research applications. The polarization stage can be optimized for a particular noble gas species and particular application by the specific programming of the control electronics or computer.

27 Claims, 4 Drawing Sheets

POLARIZED GAS DELIVERY SYSTEM/METHOD

STATEMENT REGARDING PATENT RIGHTS

This invention was made with support under Contract No. PHY 9514340 awarded by the National Science Foundation. The government has certain rights in the invention.

BACKGROUND OF THE INVENTION

1. Technical Field

The present invention relates generally to a gaseous polarization process, and in particular to a method and system for delivering a polarized noble gas to a subject or sample in a manner that minimizes depolarization of the gas during its delivery.

2. Discussion

Polarized noble gases, such as $^{129}$Xe, $^{3}$He, $^{21}$Ne, $^{83}$Kr, and $^{131}$Xe, have a wide variety of present and potential medical and therapeutic applications. For example, when $^{129}$Xe gas is inhaled by a subject, it is transported from the lungs of the subject to the blood and then throughout the body before becoming concentrated in lipids and proteins of tissues such as those forming the lungs and the brain. Studies of surfaces and bulk structures of materials with polarized $^{129}$Xe or other noble gases have also been suggested. Specifically, polarized noble gases provide useful information when used in magnetic resonance imaging (MRI) applications and nuclear magnetic resonance (NMR) studies. Examples of such an application and the results thereof are reported in an article by M. S. Albert, G. D. Cates, D. Driehuys, W. Happer, B. Saam, C. S. Springer, Jr., and A. Wishnia entitled "Biological Magnetic Resonance Imaging Using Laser Polarized $^{129}$Xe", 370 Nature 199 (Jul. 21, 1994).

Known methods of polarizing noble gases incorporate a resonant light source to optically pump an alkali metal vapor. The angular momentum of photons is transferred from the light source to the alkali metal vapor atoms via cyclical resonant absorption or scattering. As alkali metal vapor atoms absorb this angular momentum, the non-polarized noble gas is introduced into the same environment. The optically pumped alkali metal vapor atoms then collide with the non-polarized noble gas atoms and transfer polarization from the alkali metal vapor atoms to the noble gas atoms. These collisions polarize certain noble gas isotopes such as those mentioned above. The alkali metal vapor atoms are typically pumped with one of any number of certain light sources, such as alkali lamps, dye lasers, Ti-sapphire lasers, argon ion lasers, and diode lasers. In addition, the noble gases may be optically pumped by a diode laser array. One particular application of the diode laser array is disclosed in issued U.S. Pat. No. 5,617,860 entitled METHOD AND SYSTEM FOR PRODUCING POLARIZED $^{129}$Xe GAS, which is hereby incorporated by reference. Diode laser arrays have also been used to polarize $^{3}$He as described by M. E. Wagshul and T. E. Chupp in an article entitled "Optical Pumping of High Density Rb with a Broad Band Die Laser and Ga:Al:As Diode Laser Arrays: Application to $^{3}$He Polarization", 40 Physical Review 4447 (1989). Another reference dealing generally with polarization of noble gases includes an article by G. D. Cates, R. J. Fitzgerald, A. S. Barton, P. Bogorad, M. Gatzke, N. R. Newbury and B. Saam entitled "Rb-$^{129}$Xe Spin Exchange Rates Due to Binary and Three-Body Collisions at High Xe Pressures," *Physical Review A*, Volume 40, Number 8, Oct. 15, 1989, pgs. 4447–4454.

While these references deal generally with the actual polarization of noble gases, the references do not specifically deal with how the gas, once polarized, is stored and delivered to a subject or sample. Polarization lifetimes vary depending on the species and isotope as well as the environmental container. For $^{129}$Xe, polarization lifetimes range from approximately ten minutes in room-temperature glass containers to several hours frozen at liquid nitrogen or lower temperatures. In biological environments, $^{129}$Xe lifetimes are a few to tens of seconds. In addition components such as lasers and specially designed polarization chambers are required to realize the polarization process. As a result, the expense associated with polarizing, storing and delivering noble gases is typically quite high.

SUMMARY OF THE INVENTION

The present invention contemplates a system, and corresponding methodology, for producing, accumulating and delivering a polarized noble gas in a highly efficient manner and a manner that minimizes depolarization of the gas during delivery to a subject or sample. Additionally, gas can be delivered in single doses, or at constant flow rates, and can be easily automated with computer or microprocessor control. The present invention is designed to be utilizable in a clinical environment for both animal and human in vivo studies and, when coupled with an optical pumping system using a laser diode array for producing polarized $^{129}$Xe gas, minimizes overall system cost and expense.

A first preferred embodiment of the present invention provides a system for delivering a polarized noble gas to a subject for inhalation. The system includes a possibly cryogenic vessel for accumulating a polarized noble gas and a storage cylinder for storing a polarized noble gas, such as $^{129}$Xe or $^{3}$He. The system also includes a gas delivery line for delivering the polarized noble gas to the storage cylinder and then from the storage cylinder to the subject or sample. A vacuum line is in communication with the gas delivery line and evacuates the cryogenic storage vessel, the gas storage cylinder and gas delivery line prior to the polarized noble gas being delivered. A plurality of non-metallic gas delivery valves, which are either manual or automated and are preferably made from either teflon or glass, are located between the gas delivery line and the vacuum means for selectively controlling communication between the vacuum means and the polarized noble gas to minimize depolarization of the polarized noble gas during delivery of the gas to the subject.

A second embodiment of the present invention provides a method of delivering the polarized noble gas to a subject for inhalation and includes the step of evacuating a noble gas storage chamber and a gas delivery line associated therewith through a vacuum line in communication with the gas delivery line. After the gas storage chamber and delivery line are evacuated, the vacuum line is isolated from the gas delivery line through selective closing of a plurality of non-metallic valving to minimize depolarization of the polarized noble gas. Subsequently, the polarized noble gas is delivered to the storage chamber, and delivery of the gas to the storage chamber is electronically controlled to ensure delivery of the gas to a subject in a measured amount.

These and other various advantages and features of the present invention will become apparent from the following description and claims, in conjunction with the appended drawings.

DETAILED DESCRIPTION OF THE PREFERRED EMBODIMENTS

Figure 1:
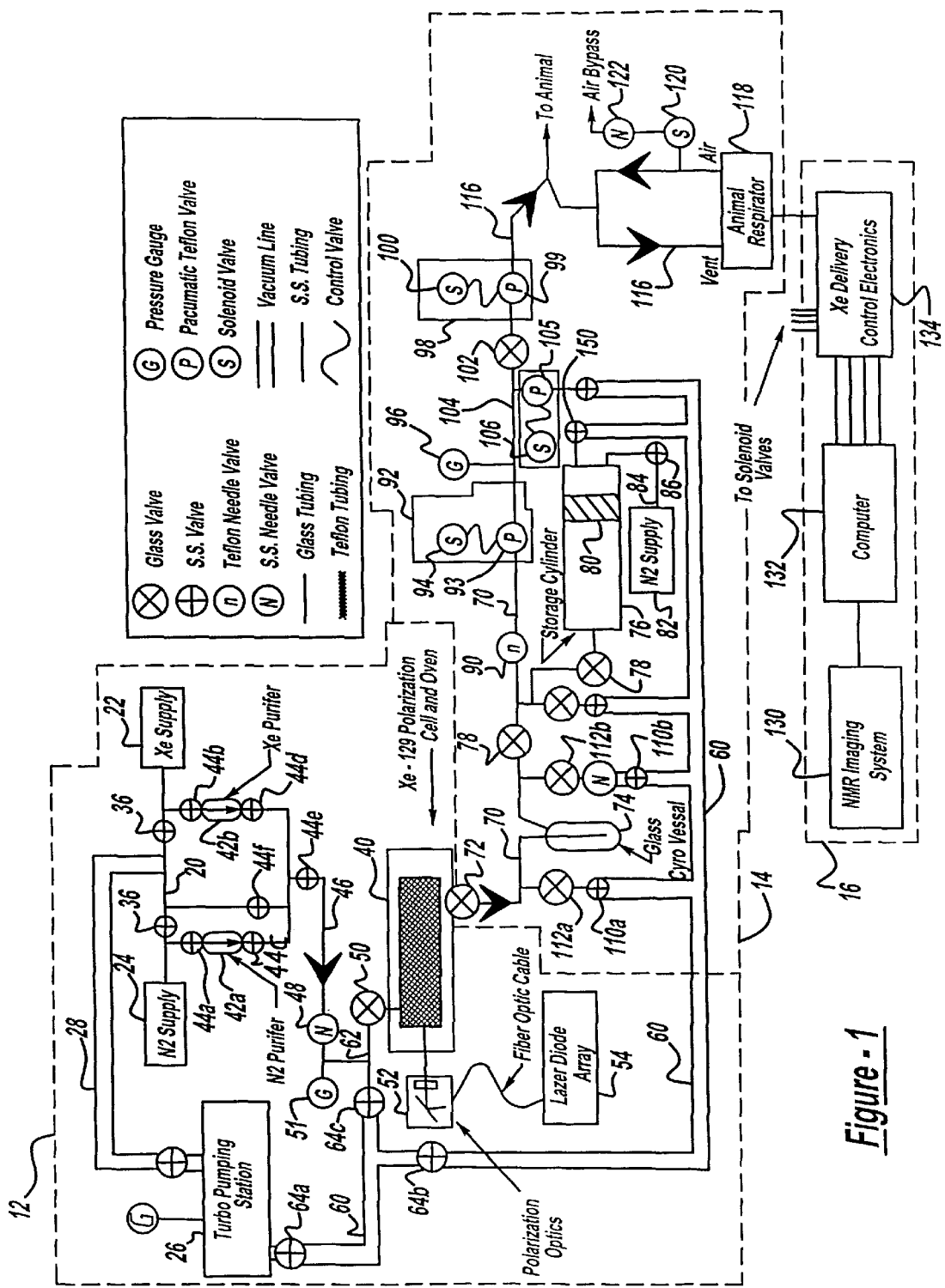
FIG. 1 is a detailed schematic diagram of the noble gas polarization and delivery system according to a preferred embodiment of the present invention.

Referring to FIG. 1 of the drawings, a detailed schematic diagram of a noble gas polarization and delivery system is shown generally at 10. Preferably, the system is utilized to polarize noble gas and deliver the polarized gas to a subject for MRI/NMR imaging related purposes. It is contemplated that the system 10 can be utilized in clinical or research environments, as the system allows a large enough volume of polarized noble gas to be produced for human clinical applications, and as a high percentage of the gas polarization is actually delivered, due to the minimal depolarization of the gas during delivery of the gas through the system. The utilization of this system in high magnetic fields requires remote actuation of valves by mechanical or pneumatic means. Additionally, polarized noble gas is delivered in metered amounts and, for biomedical applications, can be automatically mixed with oxygen as desired. The system is ideally situated in or near the fringe magnetic field of the MRI/NMR machine which provides the axis of quantization for optical pumping and the high magnetic field necessary for polarized frozen noble gas storage. Additionally, the absence of large transverse magnetic gradients minimizes noble gas depolarization during transport from the system to the subject. All materials and devices in the system are not only compatible with the transport of polarized noble gases but are also suitable for use in the high field environment of the MRI/NMR machine.

The system 10 includes three main sub-systems: A noble gas polarization sub-system 12; a noble gas storage and delivery sub-system 14; and an electronic control sub-system 16. The structure and function of each of these subsystems will be described in detail.

The noble gas polarization sub-system 12 includes a gas supply line 20 coupled to a noble gas supply 22, preferably containing xenon gas, and a buffer gas supply 24, preferably containing nitrogen. The gas supply line 20 is connected to a robust pumping station, preferably a turbomolecular pump 26, via a vacuum line 28. The turbo pumping station functions as a vacuum source for the delivery system as described below. Preferably the vacuum pumping station 26 evacuates the gas supply lines 34 when valves 36 are opened via the control electronics sub-system 16. The gas supply line 20 is also coupled to a polarization cell and oven 40 through purifiers 42a, 42b, valves 44, and a gas supply line 46. The gas supply line 46 includes a needle valve 48 and a non-metallic valve such as a teflon or glass valve 50. A pressure gauge 51 is coupled to the control electronics subsystem 16 and is located adjacent the needle valve 48 to detect noble gas/nitrogen gas pressure in line 46.

The polarization cell and oven 40 is operatively coupled to polarization optics 52 and an associated optical pumping source 54, which is preferably a laser diode array such as that utilized in issued U.S. Pat. No. 5,617,860 which has been incorporated above by reference. The gas supply line 46 is also selectively connected to the turbo pumping station through a vacuum line 60 through a high-vacuum valve 64 selectively opened and closed in response to commands from the control electronics sub-system 16.

Still referring to FIG. 1, the noble gas storage and delivery sub-system 14 is coupled to the polarization sub-system 12 via polarized gas storage delivery line 70 and a non-metallic valve 72. The non-metallic valve 72, as with all non-metallic valves utilized in the system, is substantially non-magnetic, excluding such materials as iron and stainless steel. The storage and delivery sub-system 14 includes a gas cryogenic vessel 74 for freezing and/or storing polarized noble gas delivered from the polarization cell and oven 40 until a time at which the polarized gas is required to be delivered to the subject. The cryogenic accumulation vessel 74 is preferably a pumping vessel having a volume of approximately five cubic centimeters. However, the volume of the vessel may vary according to the particular application. The accumulation vessel is coupled via the polarized gas delivery line 70 to a storage cylinder 76 through non-metallic valves 78. The storage cylinder 76 is preferably a one liter or larger non-metallic (preferably glass) cell and includes a piston 80 which is preferably, for example, a three inch diameter Teflon valve. A pressurized gas supply such as nitrogen is connected to the storage cylinder via a supply line 84 and valve 86 for selectively pressurizing the cylinder as will be described in more detail below.

Additionally, a vacuum line is connected to the storage cylinder 76 for moving the piston 80. The sub-system 14 also includes a non-metallic needle valve 90 in the gas delivery line 70 that functions to provide variable gas conductance to optimize gas delivery rates. The valve 90 may be manually or pneumatically controlled. A valve set 92, which consists of a pneumatic teflon or glass valve 93 and a solenoid activated valve 94 that actuates the pneumatic valve 93, is actuated by the control electronics subsystem to allow polarized noble gas to flow from the storage cylinder 76 in accordance with subject delivery parameters. A pressure gauge 96 is located adjacent the valve set 92 to continuously compare the pressure of the noble gas being supplied from the storage cylinder to a set point pressure to control operation of the valve set 92 and valve set 98. A valve set 98, which consists of pneumatic valve 99 and a solenoid valve 100 that controls the actuation of the pneumatic valve 99, also operates to selectively supply the polarized gas from the storage cylinder to the subject in conjunction with non-metallic valve 102. A third valve set 104 is located between the first valve set 92 and the second valve set 98 and also consists of a pneumatic valve 105 and corresponding solenoid valve 106. The third valve set evacuates the ballast volume of polarized noble gas between valve 93 and valve 99 through the first and second valve sets as described below.

The noble gas storage and delivery sub-system 14 is also connected to the turbo pumping station 26 via vacuum line 60 and electronically controlled valving. In particular, stainless steel valves 110a, 110b and non-metallic valves 112a, 112b are selectively actuated by the control electronics sub-system 16 to interface the vacuum line 60 with the gas supply line 70, the glass cryogenic vessel 74 and the storage cylinder 76. Teflon valves 112a–112b are located between the valves 110a–110b respectively and the gas supply line to minimize depolarization of gas passing through the gas supply line as described below.

Still referring to FIG. 1, the storage and delivery sub-system 14 also includes subject gas delivery line 116 that couples a system/subject interface, such as a respirator 118, with the delivery sub-system 14. A solenoid valve 120 selectively is actuated to control flow of air through a needle valve 122 to the subject as an air bypass. As discussed below, the system control electronics determines if polarized gas should or should not be delivered to the subject during a particular cycle and also determines the volume of gas and the fraction or oxygen to be introduced.

Still referring to FIG. 1, the system control electronics sub-system 16 consists of two essential components: A controller 132 and delivery control electronics 134. The controller 132 is preferably either a microprocessor or conventional computer or a standalone digital/analog control unit specifically designed for the purpose. The delivery control electronics 134 preferably consists of a package of both analog circuitry, which monitors various sensors in 10 and allows for the setting of gas delivery volume, and digital circuitry, which interfaces to the respirator 118, valve set 92 and 100 and valve 120 to control actual gas delivery timing and decision making for valve actuation. Additionally, delivery control electronics can automate polarization and delivery of the gas in the optical polarization cell through control of the valve 50 and valve 72 via specific programs suitable for optimization of polarization for each noble gas species. Also, valves 64c, 48, 44f, 44d and 44c would need to be controlled to automatically fill the optical pumping cell. In particular, the delivery control electronics links the system valves to the computer to allow the computer to selectively control opening and closing of the valves in sequence such that the delivery of the polarized noble gas to the subject may be realized in accordance with the present invention.

It is contemplated that the above-described non-metallic valves may be any type of non-metallic valve, such as a glass, plastic or ceramic valve, capable of being electronically controlled by a programmed controller provided they have sufficient magnetic properties. Alternatively, both the metallic and non-metallic valves may be mechanically or manually controlled, depending upon the application.

Figure 2:
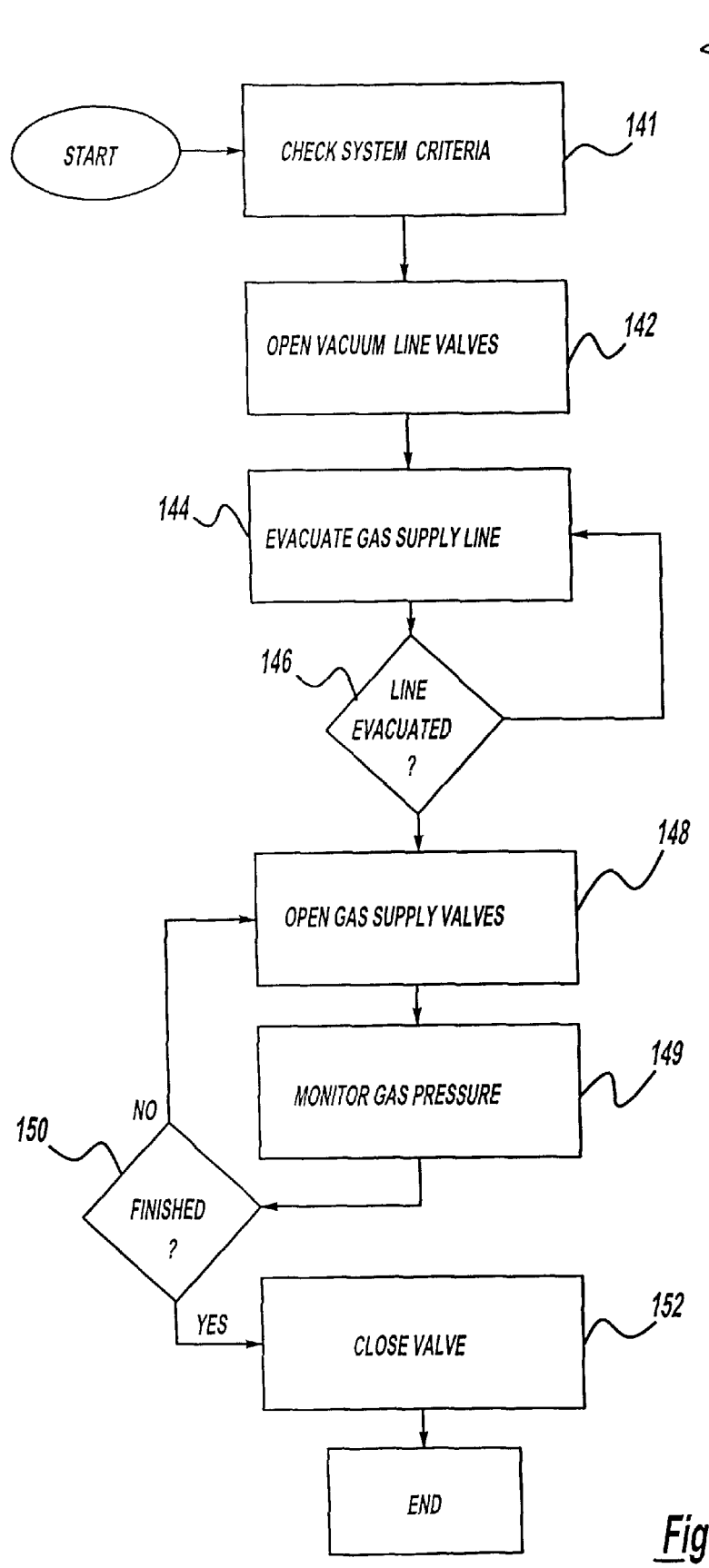
FIG. 2 is a flow diagram illustrating the methodology associated with the polarization and control electronics subsystems and shown in FIG. 1.

Referring to the flow diagrams in FIGS. 2–4, operation of the system 10 will now be described. Unless otherwise indicated, it should be assumed that all system valves are closed. Referring in particular to the flow diagram at 140 in FIG. 2, at step 141, system control criteria are evaluated by the controller. Next, the controller selectively actuates vacuum line valves 44f and 44e at step 142. At step 144, the controller activates the connection to the turbo pumping station 26 to evacuate the gas supply lines 20 via vacuum line 28. If, at step 146, the line has been evacuated, the optical pumping cell is evacuated via 50, through 64c, with 64b closed and 48 closed. The controller closes valves 44f and opens gas supply valves 44a and 44c at step 148, allowing buffer gas to flow through the gas line 46 and through the needle valve 48 to the polarization cell 40. At step 149, the controller monitors gas pressure through pressure gauge 51. At step 150, once the controller senses via the pressure gauge that a sufficient supply of buffer gas has been input into the polarization cell and oven, it closes the valve 50 at step 152. Gas supply lines 20 and 46 are then pumped out via vacuum line 28. The controller closes valves 44f and opens gas supply valves 44a and 44c at step 148, allowing noble gas to flow through the gas line 46 and through the needle valve 48 to the polarization cell 40. At step 149, the controller monitors gas pressure through pressure gauge 51. At step 150, once the controller senses via the pressure gauge that a sufficient pressure of noble gas has been input into the polarization cell and oven, it closes the valve 50 at step 152 and the noble gas is polarized by spin exchange optical pumping.

Figure 3:
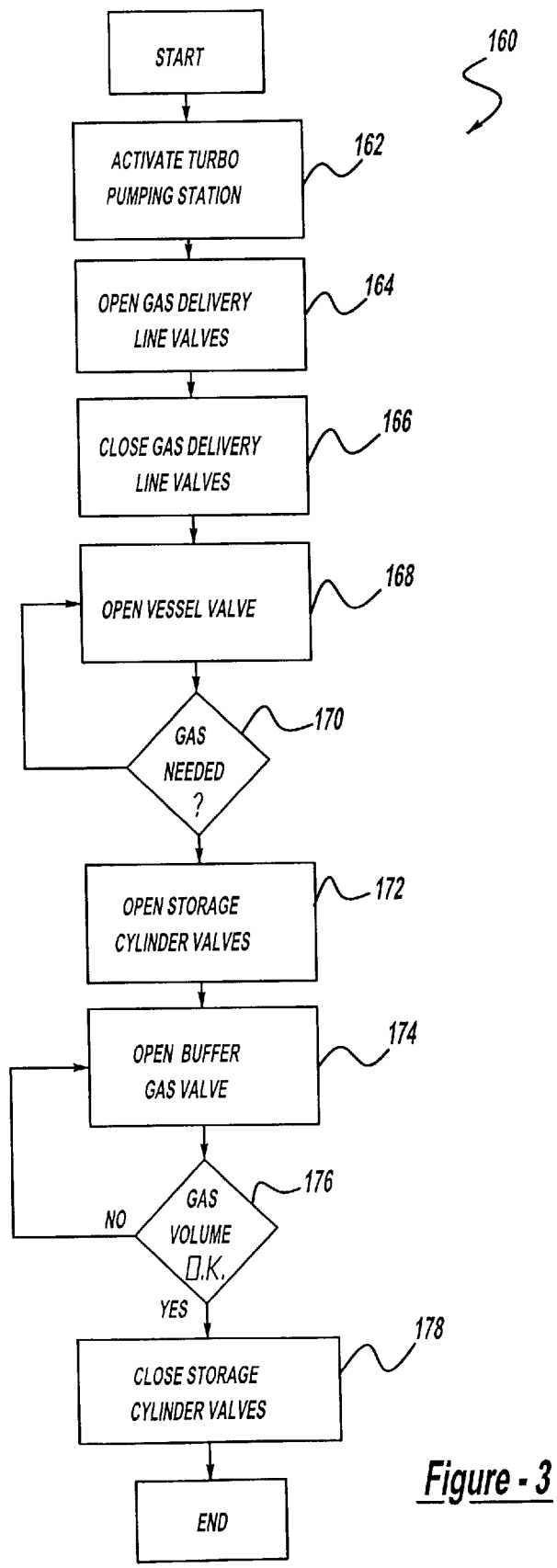
FIG. 3 is a flow diagram illustrating the methodology associated with the storage and the delivery and control electronics subsystems shown in FIG. 1.

Referring to FIG. 3, the methodology of the storage and delivery subsystem, as controlled by the controller, is shown at 160. Prior to the polarized noble gas being output from the polarization cell and oven 40 through gas delivery line 70, at step 162, the controller activates the turbo pumping station to evacuate the gas delivery line 70 through the vacuum line 60. At step 164, during evacuation, the controller opens possibly stainless steel valves 110a, 110b and corresponding non-metallic valves, as well as possibly stainless steel valves 110c, 110d. Thus, the gas delivery line 70, as well as the gas cryogenic vessel 74 and storage cylinder 76, are evacuated prior to the entry of the polarized noble gas, thereby minimizing depolarization of the gas due to exposure to other gases. At step 166, the controller closes metallic and non-metallic valves after the vessel and cylinder are evacuated. Thus, the non-metallic valves isolate the polarized gas from the metallic valves.

At step 168, after the noble gas is polarized and the line is evacuated, the controller opens the valve 72, and the polarized gas flows into the previously cooled glass cryogenic vessel 74, where it is compressed, condensed or frozen. Preferably, the vessel is maintained at a temperature of 77° K. or cooler. The gas is pumped through the cryovessel through needle valve N ensuring that the buffer gas is removed and all the noble gas is frozen. At step 170, the above methodology may be repeated, and the additional polarized gas is accumulated. Steps 162–168 are repeated as many times as necessary to produce a sufficient quantity of gas as required for a particular application. When the polarized gas is needed, the controller opens valves 78 at step 172, and the gas is unfrozen and expands into the storage cylinder 76. Once the polarized gas is unfrozen, evaporated or expanded, the valve 72 is closed. At step 174, the controller then actuates valve 150, which in turn retracts the piston 80 to the back of the storage cylinder 76. The storage cylinder is evacuated via valves 78a and 110b. At step 176, the valve 78 is opened and the cryogenic vessel warmed thereby allowing the gas to freely expand into the storage cylinder. Once the polarized gas is warmed, the valve 78 closes and the controller selectively opens the valve 86 at step 175, allowing a buffer gas such as nitrogen to flow into the storage cylinder into a volume separated from the polarized gas by the piston. The buffer gas thus maintains a constant pressure on the polarized noble gas to ensure that the gas is delivered to the subject at the desired dosage level.

Figure 4:
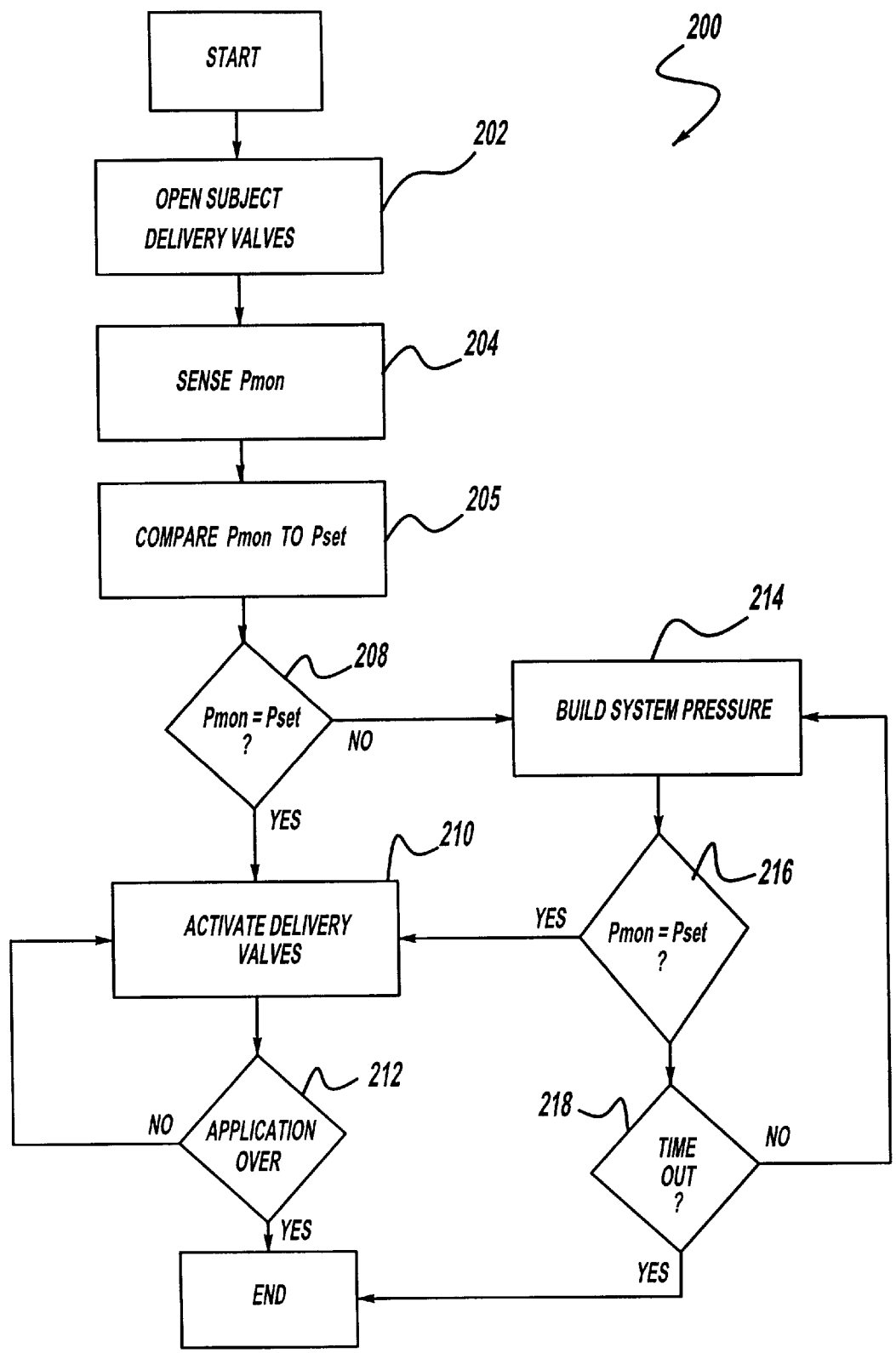
FIG. 4 is a flow diagram illustrating additional methodology associated with the storage and delivery and control electronics subsystems shown in FIG. 1.

Referring to FIG. 4, additional methodology for the delivery to a subject ventilated by a respirator of the storage and delivery subsystem, as controlled by the controller, is shown in the flow diagram 200. At step 202, during delivery of polarized noble gas from the storage cylinder to the system/subject interface 118, upon start of delivery sequence, the controller 132 actuates teflon valve 78b, thereby causing the pressurized noble gas to flow out of the delivery line 70b through needle valve 90. The controller also opens the pneumatic valve 93 via solenoid valve 94, thereby allowing the gas to flow past the pressure gauge 96 and through the teflon valve 102 through the pressure valve 99, which is opened by solenoid valve 100. The polarized gas can thus be delivered to the subject on a breath-by-breath basis in metered volume, as the pneumatically controlled valves open according to sensed pressure from the solid-state pressure gauge 96.

In particular, the delivery cycle begins upon completion of normal exhalation by the subject, and venting of the respirator 118 through the vernier needle valve 122. The needle 122 allows for precise regulation and mixing of a oxygen necessary for breathing with the oxygen/carbon dioxide mixture with the polarized gas at the subject. For animal-related applications, the respirator 118 is preferably a commercial animal ventilator respirator, which allows the polarized noble gas delivery control logic implemented at the computer 132 to be clocked by the Harvard respirator, thus allowing for cycle synchronization.

At step 204, as the gas flows through the gas supply line 70, the pressure $P_{mon}$ is sensed, or read, at the pressure gauge 96, and is continuously compared at step 205 to a target set point pressure programmed into the controller 132. If, at step 208, $P_{mon}$ equals $P_{set}$, at step 210 the controller closes the pressure valve 93 and opens the pressure valve 99 allowing the polarized noble gas to flow to the subject. The subject exhalation cycle subsequently takes place as described above, with the gas being exhausted through the respirator vent 118. At step 212, if the controller determines that the application is over, gas delivery ends. If the application is not over, gas delivery continues until the application ends.

It should be appreciated that the subject can be switched back to regular air at any time during the application by disengaging the system through opening of the pressure valve 104 at which time the current breathing cycle is finished, and the solenoid valve 120 is opened at the beginning of the subsequent inhalation cycle.

At step 208, if the controller determines that the noble gas pressure in the storage cylinder $P_{nom}$ does not reach $P_{set}$ during the inhalation cycle, the polarized noble gas will not be delivered as the pressure valve 93 will not be actuated to an open position. At step 214, the system continues to build pressure until $P_{set}$ equals $P_{nom}$ at step 216. At step 218, if the controller determines that the noble gas pressure in the storage cylinder does not reach $P_{set}$ within a predetermined number of cycles, the pressure building sequence will "time out" and return the subject to normal $0_2/CO_2$ respiration.

If at any time the noble gas pressure in the storage cylinder exceeds the predetermined set point $P_{set}$ such as may occur due to an incorrect setting in the teflon needle valve, no polarized gas will be delivered and the subject will continue normal respiration.

While the above description constitutes the preferred embodiment of the present invention, it should be appreciated that the invention may be modified without departing from the proper scope or fair meaning of the accompanying claims. Various other advantages of the present invention will become apparent to those skilled in the art after having the benefit of studying the foregoing text and drawings taken in conjunction with the following claims.

What is claimed is:

1. A system for delivering a polarized noble gas to a subject for inhalation injection or infusion, comprising:
    a storage vessel that accumulates and stores a polarized noble gas;
    a cylinder that accumulates and stores polarized noble gas and can be pressurized to produce a constant pressure polarized noble gas source;
    a gas delivery line that delivers said polarized noble gas to said storage cylinder and from said storage cylinder to the subject:
    a vacuum device in communication with said gas delivery line that evacuates said storage cylinder and said gas delivery line prior to said polarized noble gas being delivered thereto; and
    a plurality of substantially non-magnetic gas delivery valves located between said gas delivery line and said vacuum means that selectively control communication between said vacuum means and said polarized noble gas to minimize depolarization of said polarized noble gas during delivery of said noble gas to the subject on a metered basis.

2. The system of claim 1, further comprising a plurality of vacuum valves located between said vacuum device and said plurality of substantially non-magnetic valves that further selectively control communication between said noble gas and said vacuum means.

3. The system of claim 1, further comprising a controller that selectively opens and closes said plurality of substantially non-magnetic gas delivery valves.

4. The system of claim 3, further comprising:
    a cryogenic vessel that freezes said polarized noble gas before said gas is delivered to said storage cylinder;
    a substantially non-magnetic cryogenic vessel valve located between said cryogenic vessel and said storage cylinder selectively actuated by said controller that controls delivery of said polarized noble gas from said cryogenic vessel to said storage cylinder; and
    a substantially non-magnetic storage cylinder valve located in said gas delivery line between the subject and said storage cylinder selectively actuated by said controller that controls delivery of said polarized noble gas to the subject.

5. The system of claim 3, further comprising a substantially non-magnetic pneumatic valve located in said gas delivery line between said storage vessel and the subject that delivers a metered volume of said polarized noble gas from said storage vessel based on a predetermined threshold pressure level.

6. The system of claim 5, further comprising a solenoid valve selectively actuated by said controller to control actuation of said pneumatic valve in response to pressure data collected from said gas delivery line by said controller.

7. The system of claim 3, wherein said controller is programmed to compare pneumatic pressure in said gas delivery line to a threshold pneumatic delivery pressure.

8. The system of claim 1, further comprising:
    a nitrogen gas supply in communication with said storage cylinder via a nitrogen gas supply line to deliver nitrogen gas to said storage cylinder; and
    a storage cylinder piston located within said storage cylinder between said nitrogen gas supply and said polarized noble gas,
    said storage cylinder piston and said nitrogen gas supply maintaining constant pressure on said polarized noble gas for uniform dosage delivery.

9. The system of claim 1, further comprising a substantially non-magnetic needle valve positioned in said gas delivery line between said storage cylinder and the subject that controls delivery rate of said polarized noble gas to the subject.

10. The system of claim 1, wherein said plurality of substantially non-magnetic valves withhold vacuum pressure in a range of about $10^{-4}$ Torr to $10^{-6}$ Torr.

11. The system of claim 1, further comprising a one-way valve located in said gas delivery line that blocks a return flow of said polarized noble gas from the subject to said gas delivery line.

12. The system of claim 1, wherein said polarized noble gas comprises a polarized $^{129}$Xenon gas.

13. The system of claim 1, wherein said plurality of substantially non-magnetic gas delivery valves comprises a plurality of teflon gas delivery valves.

14. The system of claim 1, wherein said plurality of substantially non-magnetic gas delivery valves comprises a plurality of glass gas delivery valves.

15. The system of claim 1, wherein said plurality of substantially non-magnetic gas delivery valves comprises a plurality of ceramic delivery valves.

16. A method of delivering polarized noble gas to a subject for inhalation, comprising the steps of:
   evacuating a noble gas storage chamber and a gas delivery line associated therewith through a vacuum line in communication with said gas delivery line:
   isolating said vacuum line from said gas delivery line through at least one substantially non-magnetic valve to minimize depolarization of said polarized noble gas;
   delivering said polarized noble gas to a cylinder;
   delivering said polarized noble gas to said storage chamber; and
   electronically controlling delivery of said polarized noble gas from said storage chamber to the subject on a breath-by-breath basis.

17. The method of claim 16, wherein said step of delivering said polarized noble gas comprises:
   freezing said polarized noble gas;
   selectively unfreezing said frozen polarized noble gas; and
   delivering said unfrozen polarized noble gas to said storage cylinder.

18. The method of claim 16, further comprising the step of maintaining a constant pressure on said polarized noble gas in said storage chamber for uniform dosage delivery purposes.

19. The method of claim 16, wherein said step of delivering said polarized noble gas comprises delivering said polarized noble gas from said storage chamber to the subject based on a gas delivery line pneumatic pressure reading.

20. The method of claim 16, wherein said step of delivering said polarized noble gas comprises delivering said noble gas from said storage chamber to the subject through a plurality of remotely actuated substantially non-magnetic valves.

21. A polarized noble gas delivery system, comprising:
   a noble gas polarization cell;
   a subject delivery device in communication with said noble gas polarization cell that delivers said polarized noble gas to a subject for inhalation;
   transport tubing connected to said polarization cell that transports said polarized noble gas to said subject delivery device;
   a cryogenic cell operatively connected to said transport tubing between said polarization cell and said subject delivery device that freezes said polarized noble gas delivered from said polarization cell;
   a storage cylinder operatively connected to said transport tubing between said cryogenic cell and said subject delivery device that selectively stores unfrozen polarized noble gas input from said cryogenic cell;
   vacuum means operatively connected to said transport tubing that evacuates said polarization cell, said cryogenic cell and said storage cylinder prior to delivery of said polarized noble gas thereto; and
   a plurality of substantially non-magnetic valves located between said vacuum means and said polarization cell, said cryogenic cell and said storage cylinder that selectively isolates said polarization cell, said cryogenic cell and said storage cylinder from said vacuum means during delivery of said polarized noble gas to minimize depolarization thereof.

22. The system of claim 21, wherein said vacuum means includes a plurality of vacuum valves located between said plurality of substantially non-magnetic valves and said vacuum means that further selectively connects said vacuum means to said polarization cell, said cryogenic cell and said storage cylinder.

23. The system of claim 21, further comprising a controller that selectively activates said plurality of substantially non-magnetic valves and said plurality of vacuum valves to minimize depolarization of said polarized noble gas during transport through said transport tubing.

24. The system of claim 21, wherein said plurality of substantially non-magnetic valves comprise a plurality of teflon valves.

25. The system of claim 21, wherein said plurality of substantially non-magnetic valves comprise a plurality of glass valves.

26. A method of delivering polarized noble gas to a target comprising the steps of:
   evacuating a noble gas storage chamber and a gas delivery line associated therewith through a vacuum line in communication with said gas delivery line:
   isolating said vacuum line from said gas delivery line through at least one substantially non-magnetic valve to minimize depolarization of said polarized noble gas;
   delivering said polarized noble gas to a vessel;
   delivering said polarized noble gas to said storage chamber; and
   electronically controlling delivery of said polarized noble gas from said storage chamber to the target on a metered basis, wherein the flow of said polarized gas is controlled.

27. The method of claim 26, further comprising the step of maintaining a constant pressure on said polarized noble gas in said storage chamber for uniform dosage delivery purposes.

* * * * *